United States Patent [19]

Kochinke et al.

[11] Patent Number: 5,364,629
[45] Date of Patent: Nov. 15, 1994

[54] DEVICE AND METHOD FOR ENHANCED ADMINISTRATION OF PHYSOSTIGMINE

[75] Inventors: F. Kochinke; Richard W. Baker, both of Menlo Park, Calif.

[73] Assignee: Pharmetrix Corp., Menlo Park, Calif.

[21] Appl. No.: 682,356

[22] Filed: Apr. 9, 1991

Related U.S. Application Data

[63] Continuation-in-part of Ser. No. 506,702, Apr. 6, 1990, abandoned.

[51] Int. Cl.$^5$ .............................................. A61F 13/00
[52] U.S. Cl. ..................................... 424/449; 424/448; 514/946; 514/947
[58] Field of Search ................ 424/448, 449; 514/946, 514/947

[56] References Cited

U.S. PATENT DOCUMENTS

| | | | |
|---|---|---|---|
| 4,440,777 | 4/1984 | Zupan | 424/274 |
| 4,685,911 | 8/1987 | Konno | 604/897 |
| 4,690,683 | 9/1987 | Chien | 604/896 |
| 4,788,063 | 11/1988 | Fisher | 424/449 |
| 4,826,686 | 5/1989 | Brantl | 424/448 |
| 4,844,903 | 7/1989 | Seth | 424/448 |
| 4,965,074 | 10/1990 | Leeson | 424/449 |
| 4,973,468 | 11/1990 | Chiang | 424/449 |

*Primary Examiner*—Thurman K. Page
*Assistant Examiner*—D. Gabrielle Phelan
*Attorney, Agent, or Firm*—Anthony J. Castro

[57] ABSTRACT

Transdermal permeation of physostigmine free base and its chemical analogs are increased by the action of fatty acid esters of mono and difunctional alcohols.

12 Claims, 3 Drawing Sheets

DEVICE AND METHOD FOR ENHANCED ADMINISTRATION OF PHYSOSTIGMINE

CROSS REFERENCE TO RELATED APPLICATIONS

This application is a continuation-in-part of U.S. patent application Ser. No. 07/506,702, filed Apr. 6, 1990, now abandoned.

FIELD OF THE INVENTION

This invention is directed to devices and methods for the percutaneous administration of physostigmine free base and its closely related chemical analogs.

BACKGROUND OF THE INVENTION

Acetylcholine (ACh), an essential neurotransmitter, occurs both within the brain and in the peripheral parasympathetic nervous system. Impulses conducted along muscle fibers or axons depend upon the formation of ACh at the synaptic junction for transmission of the impulse to other fibers or axons. Acetylcholine's function as a transmitter is terminated (switched off) when it is converted to choline and acetic acid by the enzyme acetylcholinesterase (ACHE). Modern bidphysical methods have revealed that the amount of time required for the process of conversion of ACh to choline and acetic acid is less than one thousandth of a second. Drugs that have the ability to inhibit or inactivate AChE are called anticholinesterases or AChE inhibitors. As a result of AChE inhibition, acetylcholine accumulates in the synaptic cleft; and since ACh is not switched off, impulses arc transmitted to the affected site for a longer period of time and causes a stronger or more prolonged neuromuscular action. Since these ACh parasympathetic synapses are widely distributed in the brain and peripheral nervous system, it is not surprising that AChE inhibitors produce a wide variety of effects on both the brain and body. Physostigmine free base is one of the naturally occurring acetylcholinesterase inhibitors. It has been isolated from the dry, ripe seed of the calabar or ordeal bean, a perennial plant (Physostigma venenosum), found in the Calabar region of Nigeria, West Africa. Also called Esre nut, chop nut or bean of Etu Esre, calabar bean was used as an ordeal poison. As a test of guilt, the suspect was forced to ingest a quantity of calabar beans. If he died, his guilt was proved. If the accused was confident of his innocence and ate the beans rapidly, the chances were high that he would regurgitate the beans and survive the ordeal. (It is reported that proof of guilt or innocence was not always left to chance. Apparently, a placebo was given to those prejudged to be innocent by the tribal elders in order to avoid any potential miscarriages of tribal justice), see "Plants in the Development on Modern Medicine", Swain, T. ed., Harvard University Press, p. 303-360 (1972). Physostigmine free base, isolated from the calabar bean, was introduced into medicine for the treatment of wide angle glaucoma in 1877 by Laqueur. Glaucoma is a disease characterized by an increase in intraocular pressure that, if sufficiently high and persistent, can lead to damage to the optic disc and result in permanent blindness. Wide angle glaucoma, or chronic, simple glaucoma occurs when the meshwork of pores of small diameter involved in the outflow of the aqueous humor lose their tone. Wide angelo glaucoma has a gradual, insidious onset and is generally not amenable to surgical improvement. In this type of glaucoma, control of ocular pressure is only possible with continuous and permanent drug therapy.

Myasthenia gravis is a neuromuscular disease characterized by weakness and marked fatigability of skeletal muscles. Its clinical manifestations were described before the turn of the century, but it was not until the early 1930s that physostigmine was used in the management of this disease. The observation that physostigmine gave rise to increased strength of muscular contraction and the similarity between the symptoms of myasthenia gravis and curate poisoning in animals, suggested that physostigmine, an agent then known to antagonize curate, might be of therapeutic value for this disease. This observation led to the use of physostigmine in the treatment of myasthenia gravis.

Tardive dyskinesia is a disease characterized by abnormal, involuntary movements, usually of oral and facial musculature but often involving the trunk and extremities. Typical of oral and facial movements are puffing of the cheeks, grimacing, protrusion, and licking of the tongue, and incessant blinking of the eyes. The abnormal movements are rhythmic and repetitive and may interfere with speech, salivation, chewing, and swallowing. Patients, many times, are not aware of the symptoms. Tardive dyskinesia is usually irreversible and considered to be incurable, at the present time. Therefore, treatment of the symptoms of this disease is considered to be the only known possible therapy for dealing with the problem. Tardive dyskinesia is most frequently found in geriatric patients who have been taking neuroleptic drugs. All neuroleptic drugs have the potential to cause tardive dyskinesia. However, the low-dose, high potency drugs which produce the greatest degree of blockage, and thus a greater degree of pyramidal side effects are the most likely to cause tardive dyskinesia. Such high potency drugs include the phenothiazines, the thioxanthenes, the butyrophenones, the benxodiazepines, and the dihydroindolones. In recent years, the greater use of psychotropic drugs has aggravated the incidence of tardive dyskinesia. The increasing use of neuroleptic drugs in geriatric care facilities has resulted in dramatic increase in the incidence of tardive dyskinesia. See Geriatrics, Volume 34, Number 7, pages 59456, July 1979, by Harcourt Brace Jovanovich, Inc. An investigation in the use of anticholinergic drugs reported in American Journal of Psychiatry, Volume 134, Number 7, July 1979, pages 769–774 indicates that the use of physostigmine and choline have positive: therapeutic effect on tardive dyskinesia. Although the data presented is equivocal, tests have shown that physostigmine injections reduce tardive dyskinesia in from 20% to 80% of the patients suffering; from tardive dyskinesia. Continuous and permanent drug therapy is necessary to control tardive dyskinesia.

Senile dementia of the Alzheimer's type (SDAT) is a progressive, incurable, and irreversible disease characterized by long-term memory impairment. Studies in humans and animals have implicated cholinergic processes in memory functioning. Investigations with anticholinergics and cholinomimetics indicate that fluctuations in cholinergic activity can profoundly affect storage and retrieval of information in memory. Davis, et al in a study by reported in Science, Volume 201, p. 272 (1978) conclude that physostigmine significantly enhanced storage of information into long-term memory. This study moreover indicates that retrieval of information from long-term memory was also improved by physostigmine therapy. Treatment of tardive dyskinesia, wide angle glaucoma, SDAT, and the like, by injection of physostigmine is not a practical therapy. Physostigmine exhibits a short half-life (about 1 to 2 hours) due to rapid metabolism following systemic administration. Thus, treatment would require injections of physostigmine every 30 minutes to 1 hour, at a minimum, to maintain efficacious blood levels. Additionally, physostigmine has a narrow therapeutic window which necessitates constant patient monitoring for safety and can cause side effects which limit its systemic use. Recently, physostigmine has been formulated into tablets for oral dosage. Determination of drug blood levels for multiple oral doses show typical variations in blood concentration ranging from a maximum above the required level (and possibly in the toxic range) to a minimum which may be below the effective dose. The dysfunctions mentioned above, as well as many others, are more prevalent among the elderly. This population group endures more memory impairment and physical disability than other age groups and consistent therapy is necessarily, more difficult to attain. Percutaneous administration of physostigmine free base has many advantages over systemic therapy. It is well known that patient compliance is improved where therapy can be attained with a fewer number of drug applications within a twenty-four hour period. Transdermal administration offers the possibility that application of an appropriate device need occur but once in a twenty four hour period. Therapy can be terminated by simple removal of the transdermal device. Stable blood levels can be obtained using dose controlled devices, thus limiting the toxic side effects caused by overdosing and the lack of effect due to underdosing. Pharmacologically active agents with short metabolic lifetimes are particularly good candidates for transdermal drug delivery. The literature is filled with descriptions of devices for the slow or sustained or controlled release of medicaments. These devices may take the form of monolithic reservoir devices, osmotically driven devices, membrane controlled devices, enhancer controlled devices, microencapsulated drugs, bioerodable devices, and almost every conceivable combination of the above. For a general review of the art see, "Controlled Release of Biologically Active Agents", R. W. Baker, John Wiley and Sons, 1987. The transdermal delivery of systemically active drugs through the skin has certain constraints which limit its wider application. The main one is the need for very potent drugs, since, except for a few chemicals, the skin is a barrier to the passage of most substances. Thus, the most suitable drugs for controlled administration via this route are those active at a injectable dose of a few milligrams per day or less. Many cholinergic or anticholinergic drugs are effective at this dose range. The term "enhancer" as used herein is meant to include those chemical substances whose ultimate effect is to increase the amount of drug delivered to the host regardless of their modes of action. Reliable prediction of enhanced drug delivery for any given drug/enhancer combination is not possible as yet, because the many different factors that influence and control the permeation of chemicals through the skin are incompletely understood. At some point in time, the state of comprehension of skin/drug/enhancer interaction will be such that the performance of any given drug/enhancer combinations may be predictable from first principles but until that time, the designer of transdermal drug delivery devices must use empirically derived knowledge and examples. Leeson, in U.S. Pat. No. 4,575,539, (herein incorporated by reference), suggests the use of five chemically distinct enhancers ("azone", ethanol, dimethylsulfoxide, decyl methyl sulfoxide, and N-methyl lauramide) with four types of pharmaceutically active tertiary amines. Fischer, et al. (herein incorporated by reference), in U.S. Pat. No. 4,788,063, combines the free base form of a group of pharmaceutically active tertiary amines, almost identical to those described in Leeson above, with an excess of low molecular weight fatty acid which serves as both solvent and as transdermal delivery agent. Konno, et al. in U.S. Pat. No. 4,685,911, (herein incorporated by reference), describes the use of a suppository base, e.g. triglyceride of a vegetable saturated fatty acid having 12 to 18 carbon atoms in combination with a penetration enhancer. Our invention discloses the unexpected increase of skin permeability of a similar class of pharmaceutically active tertiary amines in their free base form through the use of fatty esters, especially isopropyl myristate and the ester of ethylene glycol and myristic acid. The term "low molecular weight" as used in reference to the ester type enhancers of this invention are defined as the reaction product of mono or difunctional functional alcohols containing 1 to 8 carbon atoms with fatty acids and are not of the triglyceride type as described by Konno, et al. in U.S. Pat. No. 4,685,911.

OBJECTS OF THE INVENTION

It is the object of this invention to disclose novel transdermal devices for the release of physostigmine free base and its closely related analogs.

It is another object of this invention to disclose devices and methods for controlled release of compounds effective in the treatment of memory impairment, glaucoma, tardive dyskinesia, and myasthenia gravis.

It is another object of this invention to provide a means for treatment of disorders resulting from a deficiency of acetylcholine.

It is a further object of this invention to provide a means for symptomatic treatment of disorders resulting from a deficiency of acetylcholine.

Further objects of the invention will be apparent from the description of the invention to those skilled in the art.

DETAILED DESCRIPTION OF THE INVENTION

Figure 1:
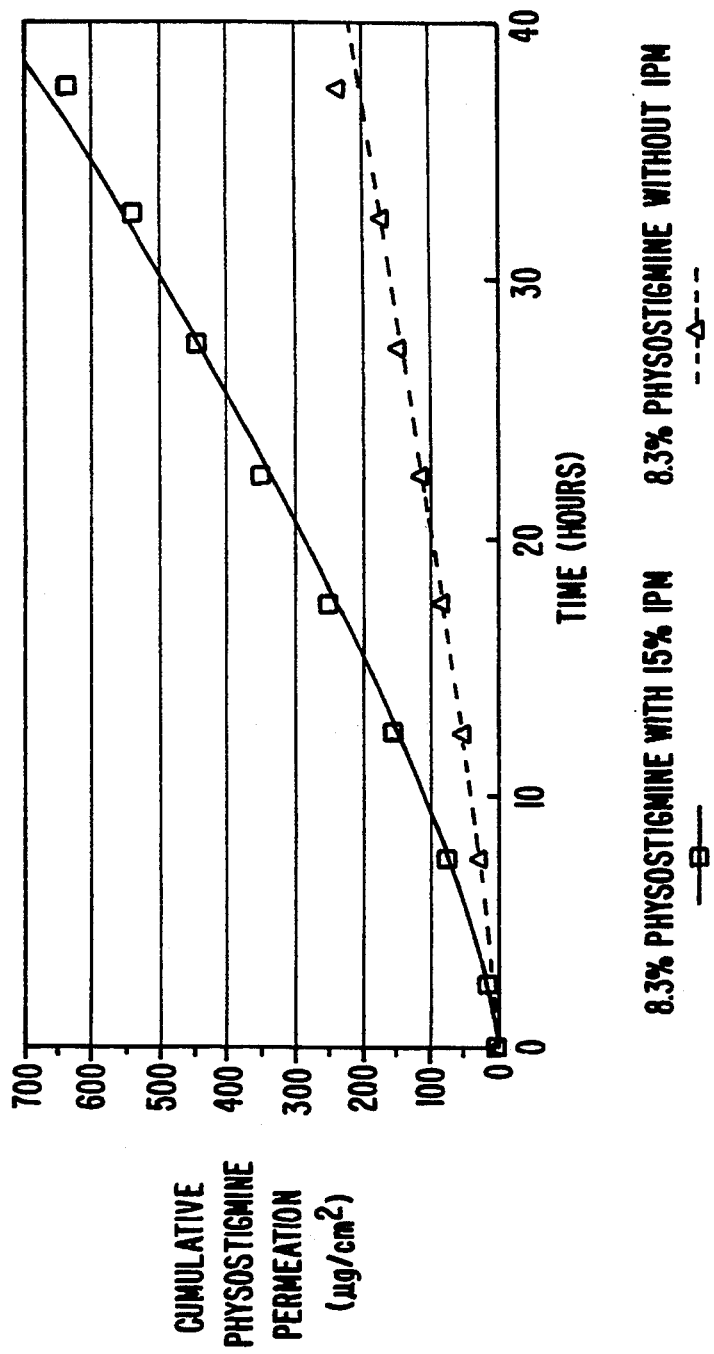
FIGS. 1-3 depict the cumulative physostigmine permeation ($mg/cm^2$) per unit time (hours) with and without IPM.

In the most elementary embodiment, a matrix loaded with physostigmine free base is first prepared by dissolving physostigmine free base and a polymer in an appropriate solvent. When a clear solution is obtained, the preparation is cast onto a protective backing by any of the techniques for polymer casting known in the art, and the solvent allowed to evaporate. After evaporation, a thin adhesive film is cast onto the matrix, or double-sided medical adhesive tape is applied to the drug matrix as a means for future attachment of the device to the target host. The adhesive is covered by a release liner and patches are cut out by punching. The finished patches may be heat sealed into foil pouches and stored until needed.

"Monolith" as used herein means a single-phase combination of chemical and polymeric carrier. One of the preferred classes of polymeric carriers are polyurethanes as described in assignee's U.S. Pat. No. 4,943,435 and U.S. Pat. No. 4,839,174 (hereby incorporated by reference). Polyurethanes are usually synthesized using polyisocyanates (hard segment) and polyols (soft segment) of various types. Many of the physical and chemical properties of a polyurethane are determined by the ratio of hard to soft segments as well as the choice of polyol and polyisocyanate reactants. Linear polyurethanes are typically made by reacting a hydroxy-terminated compound with a diisocyanate according to the reaction:

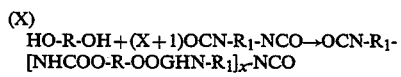

where R is a polyether, polyester, polycarbonate or hydrocarbon group, and $R_1$ is an aromatic, aliphatic, cycloaliphatic or alkyl aromatic group. The product of this reaction is an isocyanate terminated prepolymer. This prepolymer can then further reacted (two shot process) with a lower molecular weight diol (chain extender) such as 1,4-butane diol to produce linear, thermoplastic and solvent soluble elastomer. Alternatively, all the reactants can be combined in one step (one shot process) to produce the desired product. Polyether soft segmented polyurethanes have better hydrolysis resistance than polyester based polyurethanes but have less resistance to oxidation and lower tensile strength; polycarbonate based soft segmented polyurethanes normally occupy a middle ground in physical and chemical properties between the polyether and polyester types. Hydrocarbon based polyols are available and can be used to prepare polyurethanes with superior oxidative and hydrolysis resistance. Aromatic, aliphatic and alicyclic polyisocyantes offer differing degrees of ultraviolet stability, moisture resistance and biocompatibility. Thus, one of ordinary skill in the art of polyurethane synthesis can select appropriate monomers for synthesis to overcome specific application problems. Polyether, polycarbonate and hydrocarbon type polyurethanes are preferred for biomedical use, because, in general, they are more inert than polyester types. Polyurethane polymers are available in grades approved for medical use from Dow Chemical, Midland, Mich. under the trade name Pellethane ™ 2363 and from Thermedics Corporation, Woburn, Mass. under the name of Teccoflex ™ EG-80A and Teccoflex ™ EG-60D. Different hardnesses are available and the softer grades are generally preferred in the context of the present invention, because they are easier to dissolve. Other polymers that can be used as the polymer matrix material include ethylene-vinyl acetate copolymers. These polymers are commercially available (Elvax, DuPont Corporation; Ultrathene, USI Chemicals, etc.) in a wide variety of grades from 2% to more than 50% vinyl acetate content. Generally, the permeability of the polymer increases with the vinyl acetate content, see Controlled Release of Biologically Active Agents, Baker, R.W., John Wiley & Sons, p 161-165. Thus, by choosing the appropriate vinyl acetate content, matrixes with appropriate release characteristic may be obtained. Other useful matrix materials include polyether block amides such as those available from Atochem Inc. under the trade name Pebax. Also useful are silicone based polymers of all types, some of which are commercially available from Dow Corning, General Electric, etc. In general, rubbery polymers are preferred for this application, although glassy polymers such as polyvinyl chloride or ethyl cellulose could be used if supplied in a form plasticized by the drug or plasticized with a pharmacologically acceptable plasticizer such as dioctyl phthalate, polyethylene glycol, butyl sebacate or the like.

Arecoline and arecoloine derivatives have the formula I as follows:

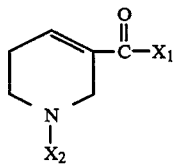

In formula I, $X_1$ represents OH, lower alkoxy, or lower alkyl, and $X_2$ independently represents H or lower alkyl.

Naloxone and naloxole derivatives may be represented by formula II as follows:

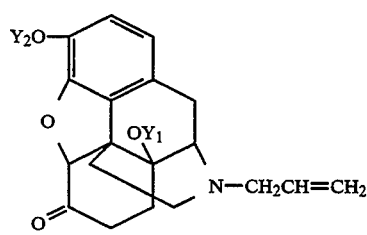

In formula II, $Y_1$ and $Y_2$ independently represent H, lower alkyl, or lower alkylcarbonyl, (acyl)-Nicotine and derivatives may be represented by formula III:

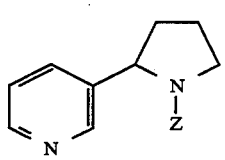

In formula III, Z represents H or lower alkyl.

The effective compounds also include physostigmine free base and physostigmine free base derivatives. Physostigmine free base and physostigmine free base derivatives may be represented by formula IV as follows:

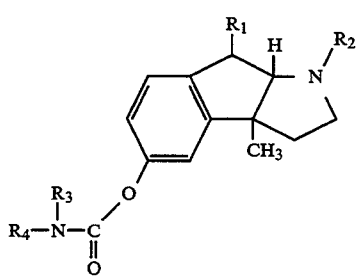

In formula IV, $R_1$, $R_2$, $R_3$, and $R_4$ independently represent H or lower alkyl. The patch may be assembled by any of the techniques known in the art for laminating patches.

Typically the first step in preparation of monolithic patches is to prepare a solution of the polymer matrix material. Solvents that may be used to dissolve polyurethane include tetrahydrofuran (THF), Fischer Scientific, Springfield, N.J., dimethylsulfoxide (DMSO), and dimethylformamide (DMF). Among these, tetrahydrofuran is the preferred solvent, because it has been approved for use with medical materials so long as the residue remaining in the material after drying does not exceed 1.5%. Typically the percentage by weight of polyurethane in the solution will be in the range 5% to about 35%, depending on the solvent and the polyurethane grade. Using THF, it is possible to prepare casting solutions with relatively high concentration, typically around 20 to 25%, of a soft grade polyurethane. The harder grades are more difficult to dissolve. It is usually desirable to make the concentration of polyurethane as high as possible to facilitate casting. Solid physostigmine free base is added to the polymer solution, and the mixture stirred until complete solution is achieved. The percentage of physostigmine free base in the solution may be varied according to the desired loading of the finished matrix. The physostigmine free base content of the finished matrix may vary widely, from around 3% to about 30%. Loading above 30% to levels of about 70% may be achieved, but because of the potency and toxicity of physostigmine free base, highly concentrated matrixes do not offer advantages that outweigh the hazards associated with accidental overdosing of physostigmine free base. Rate controlling membranes may be used to construct devices for prolonged duration therapy when high levels of drug are contained in the Matrix. Transdermal drug delivery devices may be constructed by successive application of layers or may be prepared in a more continuous fashion according to the description found in assignee's patent application Ser. No. 450,409, filed Dec. 14, 1989 and herein incorporated by reference.

Physostigmine free base in polyurethane was chosen as a model compound for the examples given but one of ordinary skill in the art can apply the general principles and methods to other analogous chemicals, adhesives, protective backing materials, release rate controlling membranes and the like.

EXAMPLE I

Transdermal physostigmine free base release patches wherein the drug and enhancer were contained within a monolithic polymer matrix with a slight amount of enhancer contained in the adhesive layer were made as follows:

Solvent soluble thermoplastic polyurethane available from Dow Chemical Co, Midland, Mich. Pellethane TM 2363-80A (24.4 gm), physostigmine free base (2.903 gm), isopropyl myristate (IPM) (2.941 gm), and tetrahydrofuran (101.3 gm) were placed in a glass vessel, sealed, placed on a roller mill and stirred overnight. Stirring was discontinued and the entrappeal bubbles allowed to rise and escape leaving a clear, colorless solution. The clear solution was then cast upon a film occlusive backing of 3M film, 3M-1109, by means of a 2000 μm rolling bar and allowed to dry overnight. The final dry film thickness was measured to be 240-300 μm. In a separate step, an adhesive/enhancer system was prepared by adding sufficient isopropyl myristate to a 40 wt% solution of Avery adhesive 460HPX in hexane, isopropyl alcohol, and toluene, to obtain an adhesive solution with 10 wt% IPM concentration in the dry adhesive film. The adhesive/enhancer system was cast onto the fluoropolymer coated side of a sheet of 3M-1022 release liner with a 200 μm casting bar. The final film thickness of this layer was 80 μm after drying under a glass plate overnight. The layer of the polymer/drug film most distal from the backing was contacted with the adhesive surface of the adhesive/polymer system to form a single laminated composition. Round sections, 1.25 inch in diameter, were punched out of this laminate to produce 7.92 cm$^2$ assemblies. These punched assemblies were placed between two square sections of 3M-1022 release finer and stored in individual low density polyethylene, foil-lined pouches.

EXAMPLE 2

Skin permeation was determined using a Crown Glass Teflon How-Through Diffusion Cell (Microstat cassette pump, flow through cells and an Isco Retriever IV automatic sampler). Freshly thawed cadaver skin rounds were punched out and placed in the apparatus. The Teflon collar was screwed on to seal the edges of the skin sample and prevent leakage around the edges of the skin. The matrix, patch or system to be evaluated was placed upon the stratum corneum side of the skin. Permeate samples were collected at regular intervals. In this manner, the permeation of physostigmine free base through skin was measured for systems prepared according to the procedure described in Example 1 containing 8.3 wt% physostigmine free base and 15 wt% isopropyl myristate and 8.3 wt% physostigmine free base without isopropyl myristate. The results are shown in Table I. As can be clearly seen from the relative physostigmine free base permeation results, isopropyl myristate significantly enhances the permeation rate of physostigmine free base.

TABLE I

| | Physostigmine free base cumulative permeate ($\mu g/cm^2$) | |
| --- | --- | --- |
| Time (Hours) | 8.3% Physostigmine free base 15% IPM | 8.3% Physostigmine free base 0% IPM |
| 0.0 | 0.0 | 0.0 |
| 2.5 | 16.1 | 9.5 |
| 12.5 | 153.2 | 50.1 |
| 17.5 | 247.6 | 81.2 |
| 22.5 | 348.1 | 112.9 |
| 27.5 | 444.7 | 145.1 |
| 32.5 | 541.2 | 169.8 |
| 37.5 | 637.7 | 233.0 |

Graphical representation of this data is shown in FIG. 1. The permeation of physostigmine free base without IPM enhancer was at a rate of about 130 $\mu g/cm^2$·day as contrasted with permeation of about 457 $\mu g/cm^2$·day obtained with 15% IPM.

EXAMPLE 3

The relative effect of different drug levels and enhancer levels in transdermal physostigmine free base release patches wherein the drug and enhancer are contained within a monolithic polymer matrix were evaluated as follows:

Solvent soluble thermoplastic polyurethane available from Dow Chemical Co, Midland, Mich., Pellethane TM 2363-80A, sufficient physostigmine free base and isopropyl myristate to achieve the desired concentrations and tetrahydrofuran were placed in a glass vessel, sealed, placed on a roller mill and stirred overnight. Stirring was discontinued and the entrappeal bubbles allowed to rise and escape leaving a clear, colorless solution. The clear solution was then cast upon a film occlusive backing of 3M film, 3M-1109, by means of a 2000 μm robing bar and allowed to dry overnight. The final dry film thickness was measured to be 240–300 μm. A solution of Dow Corning BioPsa adhesive x72920 was cast onto the fluoropolymer coated side of a sheet of 3M-1022 release liner with a 200 μm casting bar.

The final film thickness of this layer was 80 μm after drying under a glass plate overnight. The layer of the polymer/drug film most distal from the backing was contacted with the adhesive surface of the adhesive/polymer system to form a single laminated composition. Round sections, 1.25 inch diameter, were punched out of this laminate to produce 7.92 cm² assemblies. These punched assemblies were placed between two square sections of 3M-1022 release liner and stored in individual low density polyethylene, foil-lined pouches.

Figure 2:
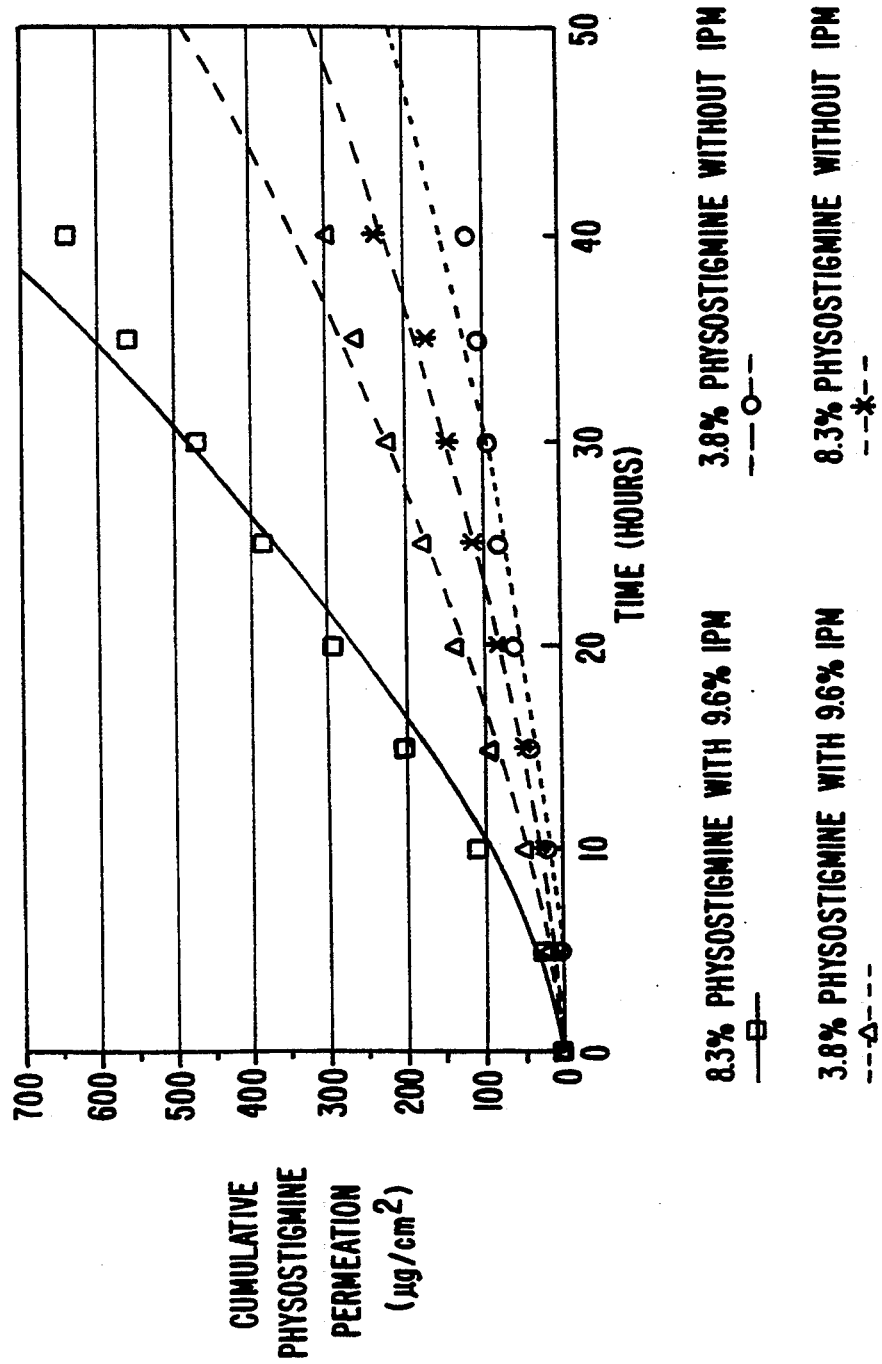

Skin permeation rate were measured according to the procedure described in Example 2 and shown in Table II. Graphical representation of this data is shown in FIG. 2.

TABLE II

| Time (Hours) | Physostigmine free base ratio cumulative permeate ($\mu g/cm^2$) | | | |
|---|---|---|---|---|
| | Physostigmine free base/IPM | | | |
| | 8.3%/9.6% | 3.8%/9.6% | 3.8%/0% | 8.3%/0% |
| 0 | 0.0 | 0.0 | 0.0 | 0.0 |
| 5 | 26.8 | 11.9 | 3.9 | 9.5 |
| 10 | 108.7 | 47.1 | 20.6 | 26.9 |
| 15 | 202.4 | 90.5 | 40.2 | 50.1 |
| 20 | 292.7 | 134.7 | 60.4 | 81.2 |
| 25 | 383.1 | 176.6 | 78.7 | 112.9 |
| 30 | 469.8 | 219.9 | 93.9 | 145.8 |
| 35 | 559.5 | 260.4 | 105.0 | 169.8 |
| 40 | 639.8 | 294.9 | 118.6 | 233.5 |

EXAMPLE 4

Figure 3:
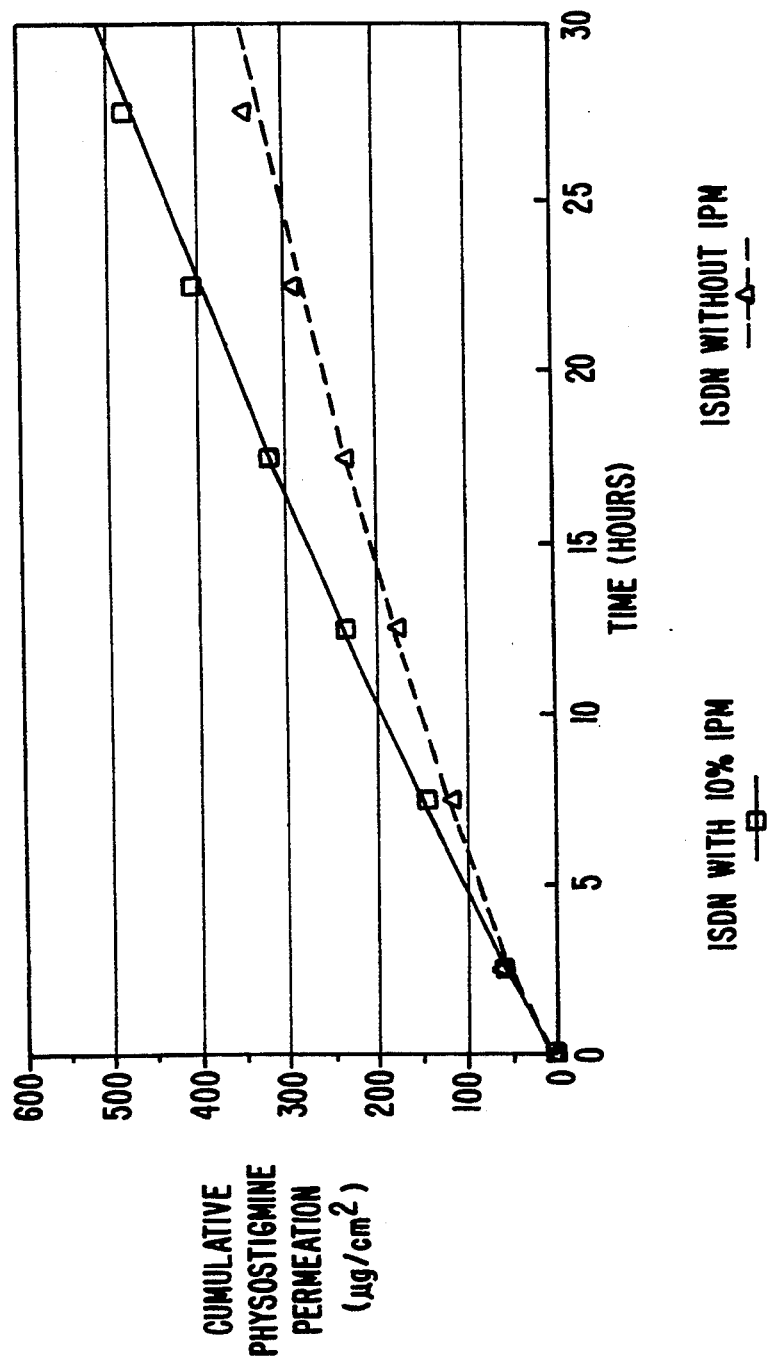

Comparative enhancement of isosorbate dinitrate by IPM was performed according to the methods described in Example 1 for the preparation of the patch and Example 2 for testing of the patch for determining if IPM enhancement of physostigmine free base could be used to generally predict enhancement of other drugs not closely related to physostigmine free base. Skin permeation was compared to a commercially available ISDN patch sold under the trade name FRANDOL TM. As the results indicate, IPM enhancement of drug permeation cannot be reliably extended outside of the compounds that are close analogs of physostigmine free base. Skin permeation rates were measured according to the procedure described in Example 2 and are shown in Table III. Graphical representation of this data is shown in FIG. 3.

TABLE III

| Isosorbide dinitrate cumulative permeate ($\mu g/cm^2$) | | |
|---|---|---|
| Time (Hours) | 10% ISDN 10% IPM | 10% ISDN 0% IPM |
| 0.0 | 0.0 | 0.0 |
| 2.5 | 60.0 | 57.1 |
| 7.5 | 145.8 | 115.8 |
| 12.5 | 233.7 | 173.4 |
| 17.5 | 319.5 | 230.3 |
| 22.5 | 403.9 | 288.4 |
| 27.5 | 483.4 | 343.7 |

It will be apparent to those skilled in this art that modifications may be made to the embodiments or changes may be made to the embodiments as herein described which will come within the spirit of the invention and within purview and scope of the appended claims.

We claim:

1. A pharmaceutical composition for transdermal application of, as the active ingredient, a drug of high intrinsic specific activity comprising in combination said active ingredient and the ester formed by reaction of a $C_1$–$C_2$ monofunctional alcohol and a fatty acid, said active ingredient selected from the group consisting of physostigmine, naloxone, nicotine, tetrahydro-aminoacridine, arecoline, oxotremorine, pilocarpine, acceclidine, scopolamine, atropine, benztropine, aprophen, trihexylphenidyl, and benactyzine.

2. A composition according to claim 1 wherein the fatty acid ester is selected from the esters of myristic acid.

3. A composition according to claim 1 wherein the active ingredient comprises from about 3 weight per cent to about 70 weight per cent of the composition.

4. A composition according to claim 1 wherein the active ingredient is physostigmine which comprises from about 3 weight per cent to about 30 weight per cent of the composition.

5. A composition according to claim 1 wherein the said composition comprises a reservoir inner layer and a drug impermeable barrier protective film.

6. A composition according to claim 5 wherein between the reservoir and the skin there is provided a diffusion control means and a removable impermeable membrane.

7. A pharmaceutical composition for transdermal application of, as the active ingredient, a drug of high intrinsic specific activity comprising in combination said active ingredient and the low molecular weight ester formed by reaction of a $C_1$–$C_2$ di-functional alcohol and a fatty acid, said active ingredient selected from the group consisting of physostigmine, naloxone, nicotine, tetrahydro-aminoacridine, arecoline, oxotremorine, pilocarpine, acceclidine, scopolamine, atropine, benztropine, aprophen, trihexylphenidyl, and benactyzine.

8. A composition according to claim 7 wherein the fatty acid ester is selected from the esters of myristic acid.

9. A composition according to claim 7 wherein the active ingredient comprises from about 3 weight per cent to about 70 weight per cent of the composition.

10. A composition according to claim 7 wherein the active ingredient is physostigmine which comprises from about 3 weight per cent to about 30 weight per cent of the composition.

11. A composition according to claim 7 wherein said composition comprises a reservoir inner layer and a drug impermeable barrier protective film.

12. A composition according to claim 11 wherein between the reservoir and the skin there is provided a diffusion control means and a removable impermeable membrane.

* * * * *